United States Patent
Sharp et al.

[11] Patent Number: 6,086,369
[45] Date of Patent: Jul. 11, 2000

[54] ULTRASONIC DENTAL SCALER INSERT

[75] Inventors: Michael C. Sharp, Centerport; David Wuchinich, New York, both of N.Y.

[73] Assignee: Parkell Products, Inc., Farmingdale, N.Y.

[21] Appl. No.: 08/782,342

[22] Filed: Jan. 13, 1997

[51] Int. Cl.[7] ............................................. A61C 1/07
[52] U.S. Cl. ................................. 433/118; 433/119
[58] Field of Search ................................ 433/118, 119

[56] References Cited

U.S. PATENT DOCUMENTS

| | | | |
|---|---|---|---|
| Re. 30,536 | 3/1981 | Perdreaux, Jr. | 433/86 |
| 4,110,908 | 9/1978 | Cranston | 433/125 |
| 4,283,175 | 8/1981 | Nash | 433/165 |
| 4,330,282 | 5/1982 | Nash | 433/118 |
| 4,406,284 | 9/1983 | Banko | 433/119 |
| 4,505,676 | 3/1985 | Gonser | 433/119 |
| 4,820,152 | 4/1989 | Warrin et al. | 433/86 |
| 4,840,566 | 6/1989 | Leonard | 433/119 |
| 4,961,698 | 10/1990 | Vlock | 433/86 |
| 5,125,837 | 6/1992 | Warrin et al. | 433/98 |
| 5,419,703 | 5/1995 | Warrin et al. | 433/216 |
| 5,431,565 | 7/1995 | Euvrard | 433/119 |
| 5,531,597 | 7/1996 | Foulkes et al. | 433/119 |
| 5,655,906 | 8/1997 | Coss et al. | 433/119 |

OTHER PUBLICATIONS

Cavitron Catalog, p. 279, undated.

*Primary Examiner*—John J. Wilson
*Attorney, Agent, or Firm*—Hoffmann & Baron, LLP

[57] ABSTRACT

An ultrasonic dental scaler insert includes a tool coupled to a connecting body which is mechanically coupled to a transducer. When the insert is placed within an ultrasonic dental scaler device handpiece, the transducer produces ultrasonic vibrations which are transmitted to the tool via the connecting body. In order to reduce the noise generated by the operating scaler insert, the connecting body includes an elastomeric material which surrounds a portion of the connecting body. Additionally, a sleeve is provided which surrounds a portion of the connecting body providing a place to grasp the scaler insert during operation. The sleeve includes a bellows section which provides vibrational damping for the insert. Furthermore, the connecting body includes a vibration dampening bushing at an end adjacent the working tool.

17 Claims, 4 Drawing Sheets

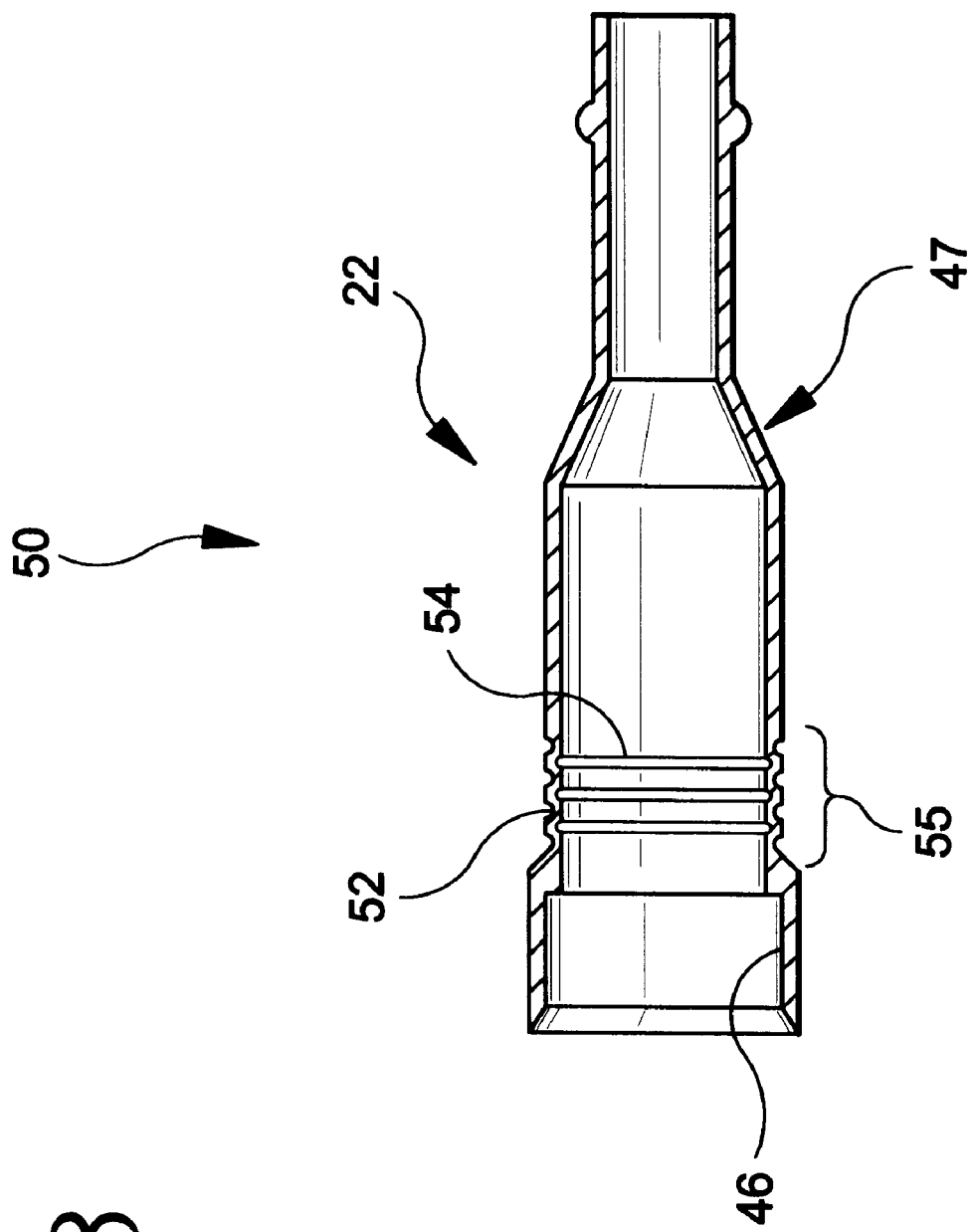

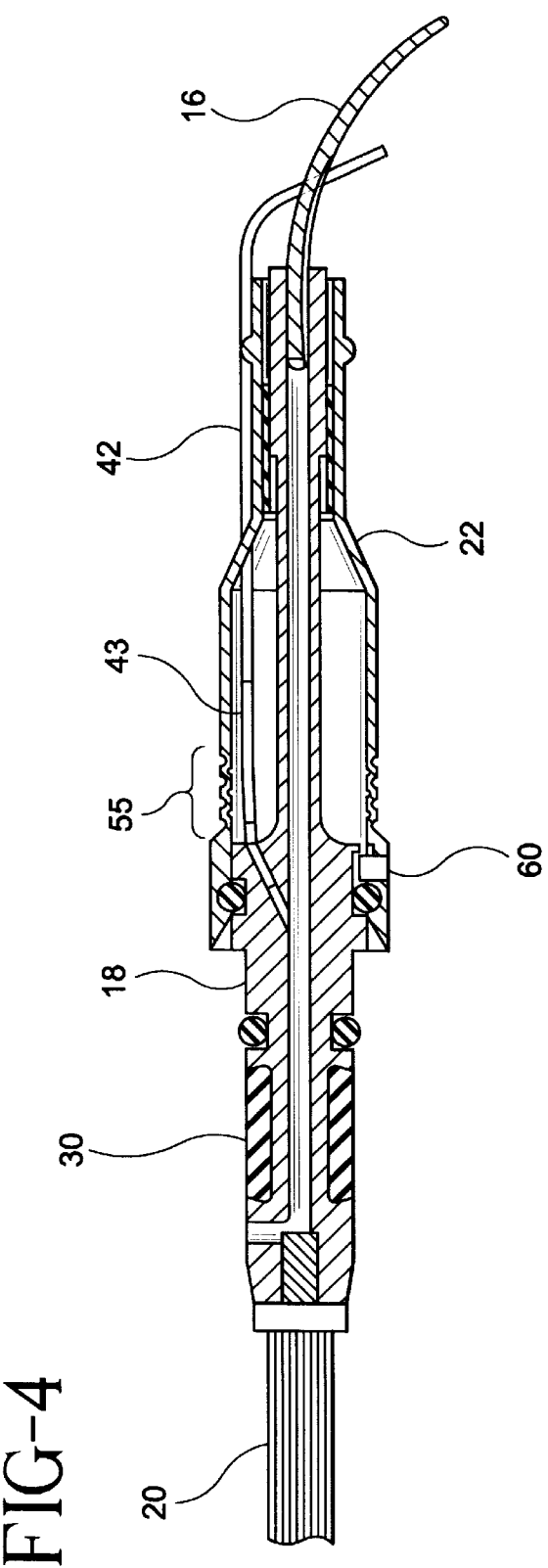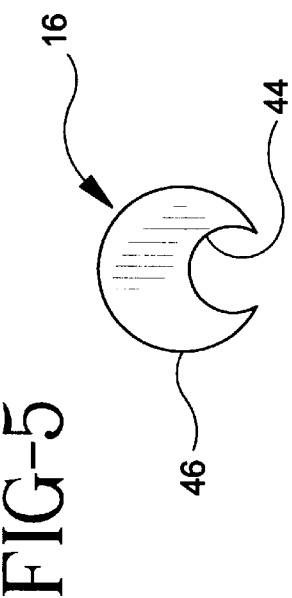

ULTRASONIC DENTAL SCALER INSERT

BACKGROUND OF THE INVENTION

1. Field of the Invention

The present invention relates to vibrating dental scaler inserts, and more particularly relates to an vibrating dental scaler insert which operates with reduced noise and dampened vibration to the scaler handpiece.

2. Description of the Prior Art

It is known in the art that plaque and calculus harbor toxic and irritating components implicated in oral disease and that plaque and calculus can be removed from teeth by high frequency scaling. Prior art scaling instruments have been designed with scaling tips that are caused to vibrate at frequencies between about 6 and 50 kHz using mechanical, magnetostrictive or piezo-electric energy.

Magnetostrictive ultrasonic dental scalers usually comprise a dental handpiece having an ultrasonic transducer positioned within an energizing coil located within a sleeve. The transducer conventionally comprises a stack of laminar plates of magnetostrictive material that is excited by the coil to longitudinally expand and contract at high frequencies.

Generally, the transducer stack is connected at one end to an acoustical impedance transformer which, in turn, is connected to a dental work tool, all of which comprises the electromechanical vibrator. The transformer provides an acoustical transmission line between the transducer and the work tool. The scaler insert is typically mounted in the handpiece sleeve by means of an o-ring.

When using magnetostrictive dental scaler inserts, heat is generated by the vibration of the laminar stacks. Accordingly, most prior art scaling devices have a conduit that transports tap water to the handpiece and onto the scaler tip for cooling thereof. In magnetostrictive devices, for example, the tap water may first be used to circulate around the transducer stack to cool the stack, and subsequently dispensed onto the scaling tip to cool the tip and irrigate the work area and cleanse the operating area of the debris.

Conventional modern magnetostrictive dental scaler inserts include a molded plastic housing surrounding the acoustical transformer portion of the insert. The plastic housing is constructed to leave an axial space around the transformer portion as the conduit for cooling water. Near the working tip of the dental scaler insert is a bushing which directs the cooling water through a groove formed in the base of the working tip and extending into the axial space within the plastic housing to provide irrigation to the operating area. The bushing near the working tip does not include any form of seal, and tends to allow the cooling/irrigating water to leak out from the end of the plastic housing. The water leaking from the end tends to drip onto the patient and also tends to cause problems with respect to generation of good water spray envelope around the working tip. Accordingly, it would be advantageous to have a dental scaler insert design in which the cooling/irrigating water is sealed within the housing preventing leakage.

A further disadvantage of conventional dental scaler inserts is the loud noise generated by operation of the insert. As is well known, most dental patients experience some degree of anxiety when visiting a dentist. Some anxiety is specifically associated with certain dental procedures such as drilling or scaling. These procedures utilize instruments having distinctive operating noises which may upset some patients merely by hearing the dental device. Thus, it would be advantageous to design a dental scaler insert which operates at a much quieter noise level to ease the anxiety of a dental patient.

Yet another disadvantage of convention dental scalers is the vibration caused by the insert which is transmitted to the handpiece of the ultrasonic dental scaler. These vibrations may cause problems to the operator of the dental scaler. Such problems include difficulty in performing procedures in which the working tip must be accurately contacted with a specific portion of a tooth or other control problems which may be encountered by the operator. For example, numbness in the hands of the operator has been noted.

A further disadvantage of conventional dental scaler inserts is associated with the sterilization of the inserts after use. Effective sterilization is best accomplished by using an autoclave. An autoclave operates under high pressure at an increased temperature to kill any bacteria on the scaler insert. Autoclave sterilization may degrade seals associated with the scaler insert as well as the molded plastic housing. This degradation may lead to leaks as discussed above with respect to the cooling/irrigating water. Accordingly, it would be advantageous to design a dental scaler insert which is highly durable and capable of withstanding an infinite number of sterilizations by autoclaving without degradation to the insert.

OBJECTS AND SUMMARY OF THE INVENTION

It is an object of the present invention to provide a dental scaler insert which is highly durable and leak-proof.

It is another object of the present invention to provide a dental scaler insert which operates at a reduced noise level.

It is yet a further object of the present invention to provide a dental scaler insert having a means for reducing vibration transmitted to the handpiece of an ultrasonic dental scaler.

It is still a further object of the present invention to provide a dental scaler insert which overcomes each of the disadvantages of conventional inserts discussed in the Background of the Invention.

In accordance with one form of the present invention, a dental scaler insert includes a working tool, a connecting body having a first end coupled to the working tool and an ultrasonic vibrating means mechanically coupled to a second end of the connecting body for causing ultrasonic vibrations to be transmitted through the connecting body to the working tool. The dental scaler insert further includes a sleeve substantially surrounding a portion of the connecting body to provide a gripping surface for the scaler insert. In a preferred embodiment, the connecting body includes a means for dampening noise generated by operation of the scaler insert.

More particularly, the noise dampening means may be in the form of an elastomeric material which surrounds a portion of the connecting body. The connecting body includes a transition region in the form of a slot or spindle of reduced diameter and the noise dampening means is positioned within the slot formed in the connecting body.

The dental scaler insert may also include a means for dampening lateral vibration transmitted from the scaler insert to the hand of an operator. The vibration dampening means may be provided on either the sleeve or the connecting body. The vibration dampening means provided on the sleeve of the insert is in the form of a bellows region positioned at a acoustical node formed by the operation of the scaler insert. The acoustical node is approximately positioned in the area where an operator holds the insert for performing dental procedures. The bellows may be formed by making grooves on either or both of the inside and outside of the sleeve to formed the vibration dampening means.

The vibration dampening means provided on the connecting body takes the form of bushing positioned around the connecting body at an end adjacent to the working tool. The bushing is preferably formed from a plastic material and substantially fills the space between the connecting body and the axial bore of the sleeve for dampening any lateral vibration which may be transmitted from the connecting body to the sleeve and ultimately to the hand of the operator. The bushing also reduces noise by damping vibration at lower harmonic frequencies which may be audible.

In a first embodiment, the dental scaler insert includes a connecting body having an axial bore therethrough and a radial bore in communication with the axial bore for providing a water inlet. The connecting body further includes an angled tap hole in fluid communication with the axial bore, the angled tap hole being coupled to a water flow jet tube for providing a supply of fluid to the working tool for forming a water envelope thereabout. The water flow jet tube may be formed from stainless steel tubing and, in an alternative embodiment, may include a section of plastic tubing positioned within the sleeve of the insert to isolate the sleeve from vibration transmitted by the connecting body to the water flow jet tube. The water flow jet tube is preferably attached to a portion of the sleeve to maintain proper positioning of the jet tube with respect to the working tool.

The connecting body and sleeve are preferably formed from stainless steel and are press-fit together to form the scaler insert. To ensure that the connecting body and sleeve are locked together, the scaler insert may include a locking pin for mechanically locking the sleeve to the connecting body and to prevent relative movement with respect to each other. The dental scaler working tool may also be formed from stainless steel and is preferably interference fit in the axial bore of the connecting body.

In yet a further embodiment of the present invention, the connecting body includes an axial bore therethrough and a radial bore in fluid communication therewith to form a fluid inlet. The working tool includes a passageway therethrough having an outlet near the tip of the working tool. The passageway is in fluid communication with the axial bore of the connecting body. Accordingly, water may be provided into the inlet through the axial bore directly to the working tool for forming a water envelope therearound.

A preferred form of the scaler insert, as well as other embodiments, objects, features and advantages of this invention will be apparent from the following detailed description of illustrative embodiments thereof, which is to be read in connection with the accompanying drawings.

BRIEF DESCRIPTION OF THE DRAWINGS

FIG. 3 is an enlarged sectional view of the sleeve portion of the dental scaler insert of the present invention.

FIG. 4 is a partial sectional side elevational view of a second embodiment of the dental scaler insert of the present invention.

FIG. 5 is an enlarged rear sectional view of the work tool of the dental scaler insert of the present invention.

DETAILED DESCRIPTION OF THE PREFERRED EMBODIMENTS

Figure 1:
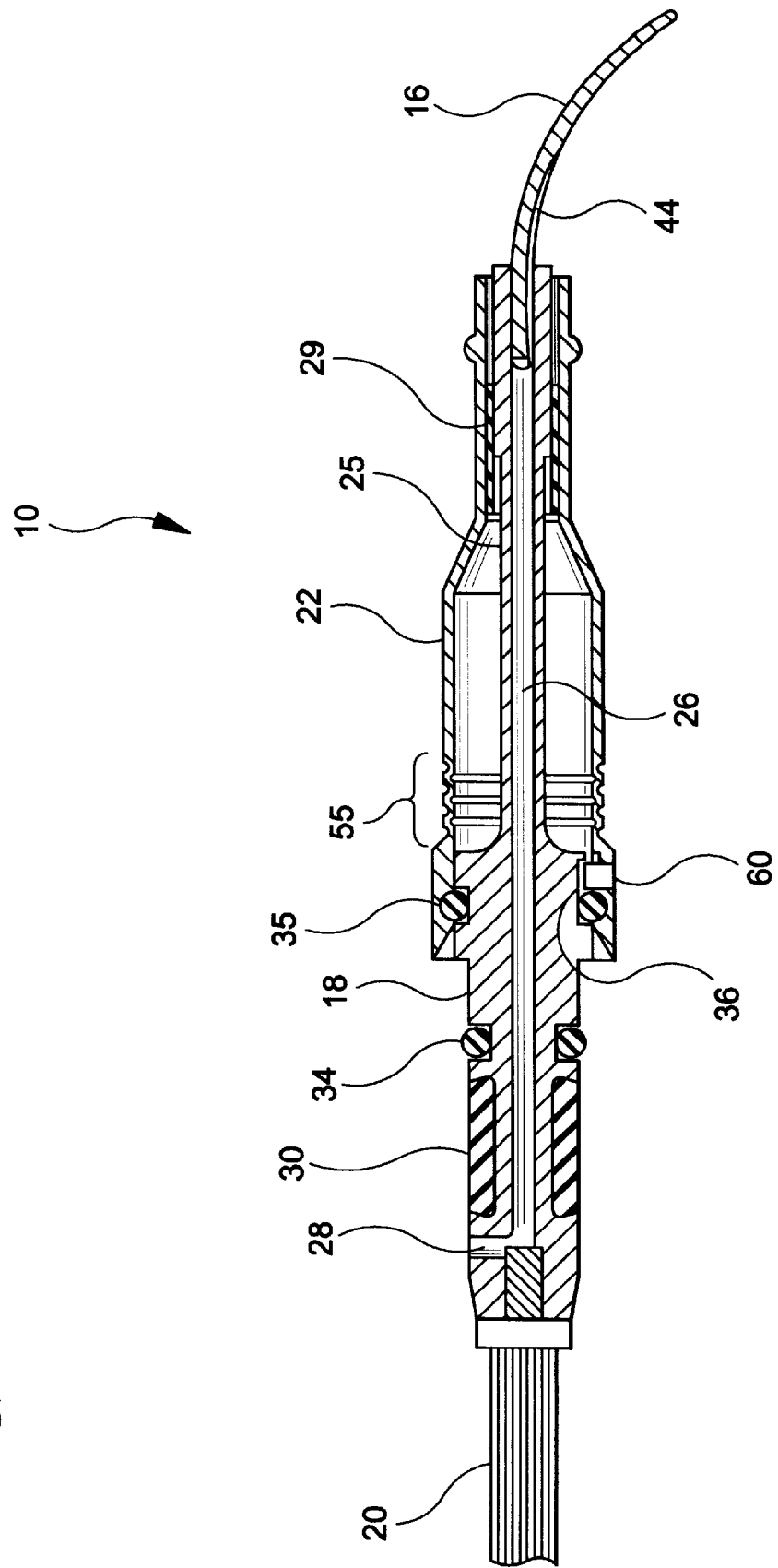
FIG. 1 is a partial sectional side elevational view of a first embodiment of the dental scaler insert of the present invention.

A vibrating dental scaler device generally includes a hollow handle assembly (not shown) for detachably receiving a dental scaler insert assembly 10. Referring to FIG. 1, the insert assembly includes a work tool 16 having a curved tip for use in dental cleaning procedures. A connecting body 18 is integrally connected at one end to the work tool 16. A vibrating means, such as a transducer 20 comprising a stack of laminar plates of magnetostrictive material are brazed or otherwise connected to the end of the connecting body 18 opposite the work tool. The scaler insert assembly 10 also includes a sleeve 22 which covers a substantial portion of the connecting body 18.

More specifically, the sleeve 22 comprises a housing which surrounds the connecting body. The sleeve 22 is dimensioned to include an axial bore therethrough having one end press fit onto the connecting body. Preferably, the point of attachment between the sleeve 22 and the connecting body 18 is at a node to minimize vibration transmission from the connecting body. A coil (not shown) is positioned within the interior space of the handle assembly to substantially surround the transducer 20. The coil may be energized by any known means thereby ultrasonically vibrating the transducer. The ultrasonic vibrations generated by the transducer 20 are transmitted through the connecting body 18 to the working tool 16.

Figure 2:
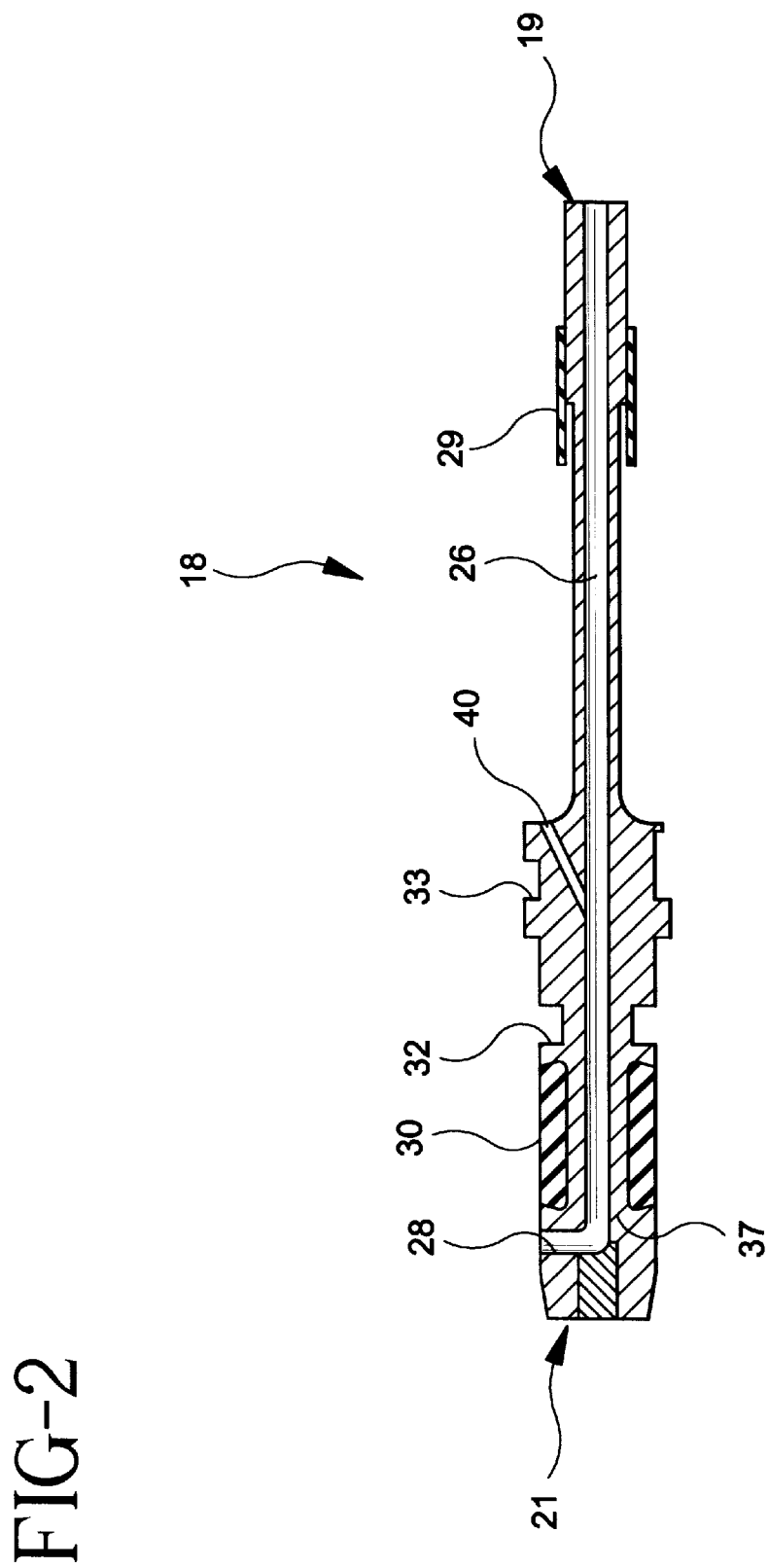
FIG. 2 is an enlarged sectional view of the connecting body of the dental scaler insert of the present invention.

The present invention provides a novel design for both the connecting body 18 and the sleeve 22 regardless of the vibrating means of the dental insert. Referring to FIG. 2, the connecting body 18 is illustrated in detail. As previously mentioned, a first end 19 of the connecting body 18 is coupled to the working tool 16. Preferably, as shown in FIG. 1, the working tool 16 is interference fit into the axial bore 26 of the connecting body. Conventionally, working tools are either soldered or threaded into the end of the connecting body. The interference fit of the working tool with the connecting body makes manufacturing of the insert easier and it simplifies the design to allow water to flow through the insert. A second end 21 of the connecting body is coupled to the transducer 20. The connecting body 18 acts as a means for transferring the vibrational motion of the transducer to the working tool.

As shown in FIG. 2, the connecting body includes an axial bore 26 through its entire longitudinal length. The central axial bore 26 provides a passageway for water which is used to form a water spray envelope around the working tool during operation. The water also provides lavage to irrigate the area of the mouth being worked on. The connecting body 18 illustrated in FIGS. 1 and 2 also includes a radial bore 28 which is perpendicular and in fluid communication with the axial bore 26. The radial bore 28 is positioned near the second end of the connecting body and comprises an irrigation inlet for an external source of water (not shown).

The connecting body 18 also includes a pair of grooves 32, 33 for housing 0-rings 34, 35 (FIG. 1). The o-ring 34 is used to provide the seal between the handle assembly and the scaler insert positioned within the handle assembly. The o-ring 35 provides sealing engagement of the connecting body to the external sleeve of the insert. O-ring 35 also isolates the sleeve from any unusual vibration which may be transmitted from the connecting body to the sleeve. A section of the connecting body 18 between the o-ring groove 32 and irrigation inlet 28 proximal to the vibration generating means 20 comprises an elongated reduced diameter portion 37. This reduced diameter portion 37 provides a housing region for a silencing means 30 which helps to reduce the noise generated by the operating ultrasonic dental scaler.

The silencing means 30 preferably comprises an elastomeric material to provide audio insulation to the dental scaler. In the preferred embodiment of the present invention, the silencing means 30 comprises an elongated silicon boot or ring positioned around and substantially filling the spindle or reduced diameter portion 37 of the connecting body producing a cylindrical, constant diameter profile along that portion of the connecting body. Thus, the silicone boot is an integral part of the acoustic system and moves with the connecting body. Traditionally, these reduced diameter portions of the connecting body do not have any material mounted therein. Accordingly, an air/water space exists between the connecting body and the handle assembly. Upon vibration of the scaler insert, noise is created in this area and vibration is transmitted to the handle assembly and ultimately the hand of the operator. The present invention reduces noise and vibration generated during operation by substantially filling and sealing the void which would exist between the narrowed portion of the connecting body and the handle assembly with a noise absorbing, vibration dampening material, such as silicon. Accordingly, noise has been measurably reduced by 6–10 dB when compared with conventional scaler inserts. Such noise reduction is both beneficial to the operator as well as to relieve anxiety of the patient.

To further reduce unwanted vibration generated by the connecting body and transferred to the sleeve, the elongated narrow portion 25 of the connecting body includes a vibration dampening means 29 in the form of a bushing surrounding the connecting body and engaging an inner surface of the axial bore of the sleeve. Referring to FIGS. 1, 2 and 4, the bushing 29 includes a pair of longitudinal ends associated therewith. The bushing is provided on the connecting body of the insert such that the longitudinal ends of the bushing are unbounded, i.e., there is no structure on either the connecting body 18 or the sleeve 22 to restrict movement of the bushing along the longitudinal axis of the insert. The bushing is slightly loose fit on the connecting body to allow the connecting body to move freely backwards and forwards but damps its tendency to move sideways suppressing unwanted transverse vibration of the connecting body in that region. These flexural or sideway vibrations in the connecting body use some of the vibratory energy and can make the motion of the tip of the working tool erratic. Furthermore, such flexural vibrations tend to be at lower harmonics and are quite audible. Accordingly, the bushing also aids to reduce the operating noise of the insert. The bushing is preferably formed of an elastomeric or plastic material. The bushing substantially fills the space existing between the connecting body 18 and sleeve 22 near the working tool end to dampen the unwanted flexural vibrations discussed above.

The connecting body 18 also includes a flange portion 36 substantially positioned around the o-ring groove 33. The flange portion provides the means on which the sleeve 22 is fit to form the insert assembly 10. In the embodiment shown in FIGS. 2 and 4, the flange portion includes an angled bore 40 having one end in fluid communication with the axial bore 26 and a second end being open for mating connection to a water jet flow tube 42 (FIG. 4). In one embodiment, the water flow tube 42 is formed from stainless hypodermic tubing which is pressed, brazed, soldered, or glued to the connecting body to be in fluid communication with angled bore 40. Alternatively, the water flow tube 42 may include a short section of plastic tubing 43 press-fit into the middle of the stainless tube. The plastic tubing 43 is positioned within the sleeve 22 of the scaler insert. The plastic tubing 43 has the effect of isolating the sleeve from any vibration transmitted from the connecting body 18 to the water flow tube 42. The portion of the water flow tube 42 which extends along the outside of the sleeve is attached to the sleeve by any known means to maintain proper positioning of the water flow tube with respect to the working tool. Accordingly, no operator adjustment of the water flow tube to obtain the desired water flow is necessary.

In an alternative embodiment illustrated in FIG. 1, the water jet tube and angled bore in the connecting body flange are eliminated. In this embodiment, the irrigation water is provided to the working tool through the axial bore 26 to the working tip at an outlet therein. Referring to FIG. 5, working tool 16 includes a slot 44 cut in the bottom portion of the base 46 of the working tool which is in fluid communication with the axial bore 26 of the connecting body when formed into the scaler insert assembly. Accordingly, water is broken up as it leaves the opening by the vibration of the working tool to form the water envelope. Since the water for the scaler insert embodiments illustrated in FIGS. 1 and 4 is provided to the working tip through a central bore in the connecting body, no leaking of fluid is possible. As discussed previously, most contemporary dental scaler inserts include a molded plastic housing having an axial space surrounding the connecting body to transfer water to the working tip. Only a bushing having no seal guides the water through a groove in the base of the working tip. Thus, these inserts tend to leak. Accordingly, the present invention solves the problem of fluid dripping from the insert onto the patient.

Referring to FIG. 3, a sectional detail of the sleeve portion 22 of the dental scaler insert assembly is illustrated. The sleeve 22 is a generally hollow tubular structure which includes a first end portion 46 dimensioned to be press-fit onto flange portion 36 of connecting body 18. The second end of the sleeve is of smaller diameter than the first end, and a transition section 47 between the first and second ends of the sleeve provides a smooth handling surface for the operator of the scaler to grasp. The first end portion 46 of the sleeve also includes a vibrational dampening means 50.

More specifically, the vibrational damping means 50 comprises a portion of the sleeve which includes at least one first groove 52 on an outer surface of the sleeve, and at least one second groove 54 within the axial opening of the sleeve 22 to form a bellows region in the sleeve. The embodiment illustrated in FIG. 3 specifically includes a series of four external grooves 52 and three internal grooves 54 positioned between each of the external grooves to form the bellows region 55. In the embodiment illustrated in FIG. 4, the bellows region only consists of the external grooves 52 on the sleeve. Alternatively, the bellows may consist of only internal grooves on the sleeve.

Additionally, the bellows region 55 is strategically placed on the sleeve to be at an acoustical node for the scaler insert. More specifically, the scaler insert is designed so that an acoustical node is formed in the area where an operator holds the scaler device. The bellows help to dampen the vibrations which are usually transmitted from the connecting body 18 to the sleeve 22 and ultimately to the hand of the operator during operation. By dampening the vibration to the scaler handpiece, the operator of the scaler device will have better control of the working tool 16 to perform the various scaling procedures.

Also illustrated in FIGS. 1 and 4, is a locking pin 60 which locks the sleeve 22 onto the flange portion 36 of the connecting body 18. Additionally, the locking pin 60 prevents relative rotation of the sleeve with respect to the connecting body and associated working tool orientation to maintain proper positioning of the component parts of the scaler insert.

The connecting body 18 and sleeve 22 of the dental scaler inserts illustrated in FIGS. 1 and 4 are preferably made from stainless steel to provide a strong, autoclavable insert, although other suitable materials such as plastic, may be used to form the sleeve. As previously noted, the transducer 20 is brazed, soldered or screwed to one end of the connecting body 18, the other end of the connecting body being in interference fit relationship with the working tool 16. Alternatively, the working tool may be brazed to the connecting body 18. The sleeve 22 is press-fit onto the connecting body 18 thereby forming a direct connection of all metal components to form the dental scaler insert of the present invention. The direct connection of all metal component parts produces an extremely strong assembly which is capable of withstanding autoclave sterilization and the rigors of the various scaling procedures. Conventional scaler inserts which include a two-piece molded plastic sleeve tend to have excessive play between the sleeve and working tool and also tend to be worn out quickly.

Accordingly, the dental scaler insert formed in accordance with the present invention overcomes many disadvantages of conventional dental scaler inserts. The present invention provides a dental scaler insert which is extremely strong due to its direct connections and being formed from stainless steel. Furthermore, the dental scaler insert of the present invention operates at a reduced noise level and with less vibration being transmitted through the insert to the operator's hand. Lastly, the scaler insert design of the present invention includes a central axial bore for supply of water to the working tool providing leak-free operation.

Although the illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A dental scaler insert, comprising:
   a working tool;
   a connecting body having a first end coupled to said working tool;
   a vibrating means mechanically coupled to a second end of said connecting body for causing vibrations to be transmitted through the connecting body to the working tool; and
   a sleeve substantially surrounding a portion of the connecting body to provide a gripping surface for the scaler insert, wherein the connecting body includes an elongated region of reduced diameter proximal to the second end of the connecting body, the scaler insert further including an elongated elastomeric material positioned around and substantially filling the reduced diameter region of the connecting body for dampening noise generated by operation of the scaler insert.

2. A dental scaler insert as defined in claim 1, wherein the elastomeric material is silicone.

3. An ultrasonic dental scaler insert as defined in claim 1, wherein one of the sleeve and connecting body includes a means for dampening lateral vibration transmitted from the scaler insert to a hand of an operator.

4. A dental scaler insert as defined in claim 3, wherein the vibration dampening means comprises a bellows region positioned on the sleeve.

5. A dental scaler insert as defined in claim 3, wherein the vibration dampening means is a bushing positioned around said connecting body adjacent an end of the working tool fitted within the connecting body.

6. A dental scaler insert as defined in claim 5, wherein the bushing is formed from plastic.

7. A dental scaler insert as defined in claim 1, wherein the connecting body includes an axial bore therethrough, a radial bore in fluid communication with the axial bore providing a water inlet and an angled tap hole in fluid communication with the axial bore, the angled tap hole being coupled to a water flow jet tube for providing a supply of fluid to the working tool for forming a water envelope thereabout.

8. A dental scaler insert as defined in claim 7, wherein the water flow jet tube includes a portion formed of plastic to isolate the sleeve from vibration transmitted by the connecting body to the water flow jet tube.

9. A dental scaler insert as defined in claim 7, wherein the water flow jet tube is mechanically attached to the sleeve to maintain proper positioning with respect to the working tool.

10. A dental scaler insert as defined in claim 1, wherein the connecting body includes an axial bore therethrough and a radial bore in fluid communication with the axial bore providing a fluid inlet, and wherein the working tool includes an angled bore through a base portion thereof, the angled bore being in fluid communication with the axial bore for providing a supply of fluid to the working tool for forming a water envelope thereabout.

11. A dental scaler insert as defined in claim 1, wherein the connecting body and sleeve are formed from stainless steel.

12. A dental scaler insert as defined in claim 1, further comprising a locking pin for mechanically locking said sleeve to said connecting body.

13. A dental scaler insert, comprising:
   a working tool;
   a connecting body having a first end mechanically coupled to said working tool;
   a vibrating means mechanically coupled to a second end of said connecting body for causing vibrations to be transmitted through the connecting body to the working tool;
   a sleeve substantially surrounding a portion of the connecting body to provide a gripping surface for the scaler insert; and
   a bushing having a pair of ends associated therewith, the bushing being positioned proximal to the first end of the connecting body, the bushing loosely surrounding the connecting body and being unbounded at either longitudinal end thereof thereby allowing the connecting body to move freely forwards and backwards with respect to a longitudinal axis of the insert and said bushing substantially filling a space between the sleeve and the connecting body for dampening transverse vibration transmitted from the connecting body to a hand of an operator.

14. A dental scaler insert as defined in claim 13, wherein the connecting body includes a means for dampening noise generated by operation of the insert.

15. A dental scaler insert as defined in claim 14, wherein the noise dampening means is an elastomeric material which surrounds and substantially fills a reduced diameter portion of said connecting body.

16. An ultrasonic dental scaler insert, comprising:

a working tool;

a connecting body having a first end coupled to said working tool;

an ultrasonic vibrating means mechanically coupled to a second end of said connecting body for causing ultrasonic vibrations to be transmitted through the connecting body to the working tool;

a sleeve substantially surrounding a portion of the connecting body to provide a gripping surface for the scaler insert; and a water jet flow tube, the connecting body including an axial bore therethrough having a water inlet associated therewith, the water jet flow tube being coupled to an outlet in fluid communication with the axial bore of the connecting body, the water jet tube having a plastic tube portion within the sleeve coupled to a metallic tube portion coupled to an external surface of said sleeve, the plastic tube portion isolating the sleeve from vibration transmitted by the connecting body to the water jet and the sleeve.

17. A dental scaler insert, comprising:

a working tool;

a connecting body having an axial bore therethrough and a first end coupled to the working tool;

an ultrasonic vibrating means mechanically coupled to a second end of the connecting body for causing ultrasonic vibrations to be transmitted therethrough; and a sleeve substantially surrounding a portion of the connecting body to provide a gripping surface for said scaler insert, wherein the connecting body further includes a bellows region positioned on the sleeve for dampening lateral vibration transmitted from the scaler insert to a hand of an operator.

* * * * *